(12) United States Patent
Lavery et al.

(10) Patent No.: US 6,254,669 B1
(45) Date of Patent: Jul. 3, 2001

(54) BLEED REDUCTION AGENTS FOR INK PRINTING INKS

(75) Inventors: Aidan Joseph Lavery, Wendover; Prahalad Manibhai Mistry, Ashton-under-Lyne; Ronald Wynford Kenyon, Bridport, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/355,846

(22) PCT Filed: Jan. 15, 1998

(86) PCT No.: PCT/GB98/00121

§ 371 Date: Aug. 5, 1999

§ 102(e) Date: Aug. 5, 1999

(87) PCT Pub. No.: WO98/34926

PCT Pub. Date: Aug. 13, 1998

(30) Foreign Application Priority Data

Feb. 5, 1997 (GB) .................................. 9702354

(51) Int. Cl.$^7$ ..................... C09D 11/02; C07D 251/54; C07D 239/48; C07D 401/00; C07D 211/90; C07D 213/61

(52) U.S. Cl. ..................... 106/31.47; 106/31.77; 544/197; 544/198; 544/208; 544/209; 544/211; 544/212; 544/218; 544/217; 544/219; 544/180; 544/298; 544/299; 544/300; 544/301; 544/302; 544/303; 544/304; 544/310; 544/311; 544/313; 544/314; 544/316; 544/317; 544/318; 544/321; 544/324; 544/325; 544/328; 544/329; 544/331

(58) Field of Search ............... 106/31.47, 31.77; 544/197–198, 208–209, 211–212, 217–219, 298–304, 310–311, 313–314, 316–318, 321, 324–325, 328–329, 331–335; 546/255, 261, 264, 268.1, 286–290, 296–297, 303–304, 307, 345

(56) References Cited

U.S. PATENT DOCUMENTS

| | | | |
|---|---|---|---|
| 4,183,929 | 1/1980 | Conrow et al. | 544/196 |
| 5,547,499 | * 8/1996 | Kawasumi et al. | 106/31.77 |
| 5,972,084 | * 10/1999 | Lacroix et al. | 106/31.47 |
| 6,048,390 | * 4/2000 | Yano et al. | 106/31.47 |

OTHER PUBLICATIONS

XP–002063056 Ink–Jet Printing Inks with Reduced Color Bleeding and Recording Therewith, Sano, Tsuyoshi et al., 6001 Chemical Abstracts, Columbus, Ohio, vol. 126, No. 06, p.718, Feb. 10, 1997, (Abstract Only).

* cited by examiner

Primary Examiner—Helene Klemanski
(74) Attorney, Agent, or Firm—Rothwell, Figg, Ernst & Manbeck

(57) ABSTRACT

A compound of the Formula (1) and salts thereof:

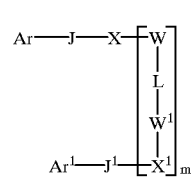

(1)

wherein:
Ar, Ar$^1$, J, J$^1$, X, X$^1$ W, W$^1$, L and m are as defined in the description. The compounds of Formula (1) are useful as additives in inks, especially ink jet printing inks, for reducing color bleed between adjacent printed regions. Also claimed are inks containing a compound of the Formula (1), a method of ink jet printing using the inks, a substrate printed with the ink and an ink jet printer cartridge containing the ink.

19 Claims, No Drawings

BLEED REDUCTION AGENTS FOR INK PRINTING INKS

The present invention relates to compounds which reduce colour bleed in ink jet printing inks and to inks incorporating such compounds.

A problem associated with certain ink jet printing processes is that colour can bleed between different coloured regions of the printed substrate. When colour bleed occurs, the boundary between adjacent coloured regions becomes indistinct or blurred, resulting in a low resolution printed image. To produce high resolution colour images using ink jet printing there is a need for inks which exhibit low colour bleed.

Prior solutions to the problem of colour bleed have involved the addition of large quantities of surfactant to the inks to enhance the penetration of the ink into the substrate used for printing. However, the presence of large quantities of surfactant in the ink may reduce the optical density of the printed image and can result in the ink being visible on the opposite side of the paper. Both of these effects reduce the print quality of the image.

EP 0,534,635 discloses a method for reducing colour bleed by using colorants which become insoluble under defined pH conditions. U.S. Pat. No. 5,198,023 discloses the use of a multivalent salt in yellow inks containing a cationic dye, the salt acting as a precipitating agent for anionic dyes contained in differently coloured inks. Both of these methods control colour bleed by causing the colorant present in an ink to precipitate when the ink contacts another ink of a different colour on the printed substrate. The degree of colour bleed reduction obtained using these methods is controlled primarily by the speed of the precipitation reaction at the interface between the differently coloured regions on the printed substrate.

According to a first aspect of the present invention there is provided a compound of the Formula (1) and salts thereof:

$$Ar-J-X-\begin{bmatrix} W \\ | \\ L \\ | \\ W^1 \\ | \\ Ar^1-J^1-X^1 \end{bmatrix}_m \quad (1)$$

wherein:
Ar and $Ar^1$ each independently is an optionally substituted aromatic group and at least one of Ar and $Ar^1$ carries at least one group selected from —COOH and —$PO_3H_2$;
J and $J^1$ each independently is —O—, —S—, —$NR^1$— or a group of the Formula (2) or (3):

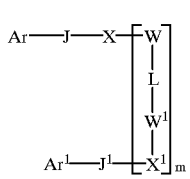

(2)

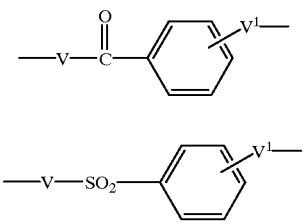

(3)

V and $V^1$ each independently is —O—, —S— or —$NR^1$—;

X and $X^1$ each independently is a group of the Formula (4), (5) or (6):

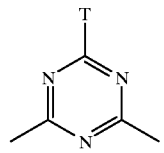

(4)

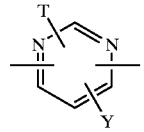

(5)

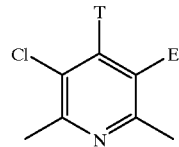

(6)

T is —$OR^2$, —$SR^2$, —$NR^3R^4$ or a labile atom or group;
Y is H, CN or T;
E is Cl or CN;
each $R^1$ independently is H or optionally substituted alkyl;
$R^2$, $R^3$ and $R^4$ each independently is H, alkenyl, substituted alkenyl, alkyl, substituted alkyl, aryl, substituted aryl, aralkyl, substituted aralkyl, cycloalkyl or substituted cycloalkyl, or $R^3$ and $R^4$ together with the nitrogen atom to which they are attached form a 5 or 6 membered ring;
W and $W^1$ each independently is —O—, —S—, or —$NR^5$—;
$R^5$ is H or optionally substituted alkyl; or the group —$NR^5$— is an optionally substituted piperazinylene group;
L is a divalent organic linking group; or
the group —$WLW^1$— forms an optionally substituted piperazinylene group; and
m is 0, 1 or 2.

Ar and $Ar^1$ are preferably optionally substituted monocyclic or polycyclic aromatic groups containing up to 10 carbon atoms and optionally contain one or more heteroatoms.

Preferred monocyclic aromatic groups are optionally substituted phenyl, pyridyl, thiophenyl and furanyl groups. Preferred polycyclic aromatic groups are optionally substituted naphthyl, quinolinyl, indolinyl, benzthiophenyl, benzofuranyl and bi-phenyl groups.

The optional substituents on Ar and $Ar^1$ are preferably selected from carboxy; halogen; —$NO_2$; —$CF_3$; —CN; —$PO_3H_2$; a $C_{1-6}$-alkyl, $C_{2-6}$-alkenyl, $C_{5-8}$-cycloalkyl or $C_{1-6}$-alkoxy group optionally substituted by —OH, —$NH_2$, —$NO_2$, —$SO_3H$ or halogen; and groups of the formula —$OR^6$, —$COR^6$; —$SR^6$, —$NR^6R^7$, —$SO_2NR^6R^7$, —$NR^6COR^7$, —$CONR^6R^7$, or —$OCOR^6$, wherein $R^6$ and $R^7$ each independently represent H, $C_{1-4}$-alkyl, $C_{5-8}$-cycloalkyl, phenyl or $R^6$ and $R^7$ together with the nitrogen to which they are attached form a 5 or 6 membered ring, preferably morpholine or piperazine.

More preferably the optional substituents on Ar and $Ar^1$ are selected from —COOH, —$SO_3H$, —$PO_3H_2$, —OH, —NH$_2$, C$_{1-4}$-hydroxyalkyl, —Cl, C$_{1-4}$-alkyl, C$_{1-4}$-alkoxy and hydroxy —C$_{1-4}$-alkoxy, provided always that at least one of Ar and Ar$^1$ carries at least one group selected from —COOH and —PO$_3$H$_2$.

It is preferred that at least one of Ar and Ar$^1$ carry at least one carboxy group.

Ar and Ar$^1$ are preferably independently selected from substituted naphthyl and substituted phenyl, especially substituted phenyl (in either case at least one of Ar and Ar$^1$ carries at least one group selected from —COOH and PO$_3$H$_2$). It is preferred that both Ar and Ar$^1$ carry at least one, more preferably two carboxy substituents. Accordingly, in a preferred embodiment of the present invention, Ar and Ar$^1$ each independently represent a group of the Formula (7):

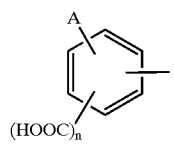

(7)

wherein:
n is 1 or 2; and
A is H, alkyl, substituted alkyl, alkoxy, substituted alkoxy, halogen, —SO$_3$H, —PO$_3$H$_2$, —OR$^6$ or —NR$^6$R$^7$, wherein R$^6$ and R$^7$ are as hereinbefore defined.

A is preferably selected from H, C$_{1-4}$-alkyl, substituted C$_{1-4}$-alkyl, C$_{1-4}$-alkoxy, substituted C$_{1-4}$-alkoxy, halogen (especially Cl), —OH, —PO$_3$H$_2$, —NR$^6$R$^7$ and —SO$_3$H. More preferably A is selected from H, C$_{1-4}$-alkyl, C$_{1-4}$-hydroxyalkyl, —SO$_3$H, —PO$_3$H$_2$, —OH, —Cl, —C$_{1-4}$-alkoxy and hydroxy —C$_{1-4}$-alkoxy. It is especially preferred that A is H.

Preferably n is 2. When n is 2, preferably the two —COOH groups are meta with respect to the groups represented by J and J$^1$ in Formula (1).

Each R$^1$ is preferably independently selected from H, C$_{1-4}$-alkyl or C$_{1-4}$-alkyl substituted by —OH, —SO$_3$H or COOH, more preferably H or C$_{1-4}$-alkyl and especially H, methyl and ethyl.

Preferably the groups represented by V and V$^1$ are each independently —O— or a group of the formula —NR$^1$—, wherein R$^1$ is as hereinbefore defined, more preferably —NH—.

When X or X$^1$ is of the Formula (5) it is preferred that T is attached to the carbon atom between the two ring nitrogen atoms and that Y is para with respect to T. It is, however, preferred that X and X$^1$ each independently is of the Formula (4).

R$^2$, R$^3$ and R$^4$ are preferably independently selected from H, optionally substituted C$_{2-10}$-alkenyl, optionally substituted C$_{1-20}$-alkyl, optionally substituted phenyl, optionally substituted phenyl-(C$_{1-4}$-alkylene) and optionally substituted C$_{5-8}$-cycloalkyl; more preferably H, optionally substituted C$_{1-18}$-alkyl, allyl, phenyl, benzyl, phenylethyl and cyclohexyl; and especially H, optionally substituted C$_{1-12}$-alkyl, allyl, phenyl, benzyl, and cyclohexyl.

Substituents which may be present on R$^2$, R$^3$ and R$^4$ are preferably independently selected from C$_{1-6}$-alkyl (preferably C$_{1-4}$-alkyl); C$_{1-6}$-alkoxy (preferably methoxy and ethoxy); halogen, (preferably Cl and Br); hydroxy; nitro; —CN; —CF$_3$; —NH$_2$, —SO$_3$H and —COOR wherein R is H, C$_{1-4}$-alkyl or phenyl. It is especially preferred that the substituents are independently selected from —OH and COOH.

R$^2$ is preferably selected from H, C$_{1-12}$-alkyl or C$_{1-12}$-alkyl substituted by —OH, carboxy or sulpho. More preferably R$^2$ is H or C$_{1-10}$-alkyl substituted by —OH, carboxy or sulpho and especially H, methyl, ethyl, n-propyl, carboxyethyl and sulphopropyl.

When T$^4$ is a labile atom or group, it is preferably an atom or group which is bound by a chemical bond to the compound of Formula (1) which is displaceable by a hydroxyl group of cellulose under mildly alkaline aqueous conditions to form a covalent bond between the compound of Formula (11) and cellulose.

Preferred labile atoms and groups represented by T include halogen atoms (preferably F and Cl); thiocyano groups; quaternary ammonium groups, for example trialkylammonium groups and optionally substituted pyridinium groups.

Preferably T is —OR$^2$, —SR$^2$, —NR$^2$R$^3$ or Cl, more preferably —OR$^2$, —SR$^2$ or —NR$^2$R$^3$ wherein R$^2$ and R$^3$ are as hereinbefore defined.

When T is —NR$^3$R$^4$, it is preferred that R$^3$ and R$^4$ are each independently selected from H, optionally substituted C$_{1-20}$-alkyl, allyl, optionally substituted phenyl, optionally substituted phenyl-(C$_{1-4}$-alkylene) and optionally substituted C$_{5-8}$-cycloalkyl; more preferably H, optionally substituted C$_{1-18}$-alkyl, optionally substituted phenyl, benzyl, phenylethyl and cyclohexyl; especially H, C$_{1-10}$-alkyl, C$_{1-10}$-hydroxy-alkyl, optionally substituted phenyl and benzyl; and more especially H, hydroxyethyl, hydroxypropyl, n-ethyl, n-propyl, n-pentyl, n-hexyl.

When R$^3$ and R$^4$ together with the nitrogen to which they are attached form a 5 or 6 membered ring they preferably form an optionally substituted morpholinyl, piperidino or piperazinyl group, more preferably morpholinyl or piperazinyl optionally substituted by C$_{1-6}$-alkyl or C$_{1-6}$-alkyl substituted by —OH, —COOH or —SO$_3$H.

It is especially preferred that T is —OH a group of the formula —NHR$^4$ piperazinyl or morpholinyl wherein R$^4$ is as hereinbefore defined. Examples of preferred groups of the formula —NHR$^4$ include n-hexylamino, n-butylamino, n-pentylamino, n-heptylamino, n-octylamino, hydroxyethylamino and carboxyethylamino.

W and W$^1$ are preferably each independently a group of the formula —NR$^5$—.

Each R$^5$ is preferably independently selected from H or optionally substituted C$_{1-4}$-alkyl, more preferably H or C$_{1-4}$-alkyl optionally substituted by —OH carboxy or sulpho and especially H, methyl, carboxymethyl, ethyl and hydroxyethyl.

When the group —NR$^5$— forms an optionally substituted piperazinylene group, it is preferably 1,4-piperazinylene which is optionally substituted by a group selected from C$_{1-4}$-alkyl and hydroxy-C$_{1-4}$-alkyl, more preferably it is a 1,4-piperazinediyl group.

The divalent linking group represented by L may be a divalent aliphatic group, a divalent aromatic group or a divalent group which contains both aromatic and aliphatic groups.

Preferably L is free from azo groups.

Preferred divalent organic linking groups represented by L are alkylene, preferably $C_{1-20}$-alkylene, more preferably $C_{2-10}$-alkylene, each of which is optionally interrupted; alkenylene, preferably $C_{2-10}$-alkenylene; arylene, preferably arylene containing up to ten carbon atoms, more preferably phenylene or naphthylene and especially 1,3- or 1,4-phenylene; aralkylene, more preferably $C_{7-12}$-aralkylene, especially phenylene-$C_{1-6}$-alkylene more especially benzylene; and two arylene groups joined together either directly or through a divalent link; each of the above divalent organic linking groups may be substituted or unsubstituted.

When the divalent linking group L is substituted, the substituent(s) is/are preferably selected from alkyl optionally substituted by hydroxy, carboxy or sulpho, preferably hydroxy-$C_{1-4}$-alkyl, carboxy-$C_{1-4}$-alkyl or sulpho-$C_{1-4}$-alkyl; alkoxy, preferably $C_{1-4}$-alkoxy and especially methoxy; phenyl optionally substituted by $C_{1-4}$-alkyl, carboxy, hydroxy, sulpho, amino or nitro; halo, preferably F or Cl; —$SO_3H$; —COOH; —OH; —CN; —$NO_2$ and $PO_3H_2$.

When L is an alkylene group it is preferably $C_{2-10}$-alkylene optionally interrupted by —O—; —S—; arylene, especially phenylene; —$NR^{10}$—; —C(O)—; —CO(O)—; or an optionally substituted piperazine group, wherein $R^{10}$ is H, $C_{1-4}$-alkyl, optionally substituted by —OH, carboxy or sulpho. When the interrupting group is optionally substituted piperazine the optional substituent(s) is/are preferably $C_{1-6}$-alkyl or $C_{1-6}$-alkyl substituted by hydroxy, carboxy or sulpho.

An especially preferred interrupted alkylene group is of the Formula (8) or, more preferably, Formula (9):

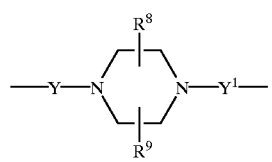

(8)

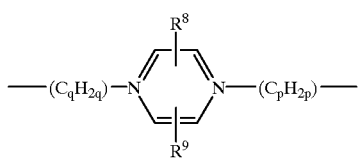

(9)

wherein:
each Y and $Y^1$ independently is optionally substituted $C_{1-10}$-alkylene;
$R^8$ and $R^9$ each independently is H or $C_{1-4}$-alkyl optionally substituted by —OH, —COOH or —$SO_3H$; and
q and p each independently is an integer from 1 to 6.

A further preferred interrupted alkylene group represented by L is of the Formula (10):

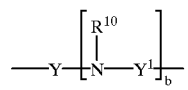

(10)

wherein:
each $R^{10}$ independently is H, $C_{1-4}$-alkyl optionally substituted by —OH, —$SO_3H$ or —COOH;

Y and $Y^1$ each independently is as hereinbefore defined; and
b is 1, 2, 3 or 4.

When Y or $Y^1$ are substituted, preferred substituents are selected from —OH, —COOH, halogen, —$SO_3H$, nitro or a group of the formula —$NR^6R^7$ wherein $R^6$ and $R^7$ are as hereinbefore defined. It is preferred, however, that Y and $Y^1$ are un-substituted.

An especially preferred group of Formula (10) is of the formula:

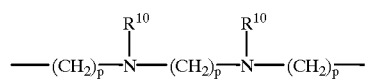

wherein each p and each $R^{10}$ independently is as hereinbefore defined.

It is preferred that $R^8$, $R^9$ and $R^{10}$ are each independently H, methyl, ethyl, propyl, hydroxyethyl, hydroxypropyl, carboxyethyl or sulphopropyl, more preferably H or methyl.

When L is arylene it is preferably phenylene or naphthylene each of which is optionally substituted.

Preferred aralkyl groups represented by L include —($C_{1-6}$-alkylene)-arylene and —($C_{1-6}$-alkylene)arylene($C_{1-6}$-alkylene)— more preferably —($C_{1-6}$-alkylene)phenylene, —($C_{1-6}$-alkylene)phenylene($C_{1-6}$-alkylene)— and especially —$C_6H_4CH_2$—, —$CH_2$—$C_6H_4$—$CH_2$— and —$C_6H_4CH_2CH_2$— each of which is optionally substituted.

An especially preferred aralkyl group represented by L is of the formula:

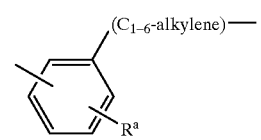

wherein:
$R^a$ is H, $C_{1-4}$-alkoxy, F, Cl, —$SO_3H$, —COOH, —OH, —CN, —$NO_2$ or $C_{1-4}$-alkyl optionally substituted by hydroxy, carboxy or sulpho.

When L is two arylene groups joined together directly it is preferably a biphenylene group, more preferably optionally substituted 4,4'-biphenylene.

Preferred arylene groups joined by a divalent linking group are of the Formula (11):

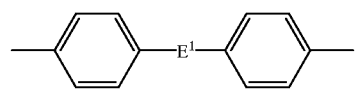

(11)

wherein:
$E^1$ is —O—, —S—, —$SO_2$—, —CO—, $C_{2-4}$-alkylene, substituted $C_{2-4}$-alkylene $C_{2-4}$-alkenylene or substituted $C_{2-4}$-alkylene, —NHCONH— or —$OCH_2CH_2O$—.

$E^1$ is preferably —O—, —S—, —CO—, —$C_{2-4}$-alkylene.

Examples of groups represented by L include:

| | |
|---|---|
| ethylene | 2-nitro-1,4-phenylene |
| 1,2- and 1,3-propylene | 4-methoxy-1,3-phenylene |
| 1,4-butylene | 4-nitro-1,3-phenylene |
| 1,5-pentylene | 2-chloro-1,4-phenylene |
| 1,6-hexylene | 3,7-disulpho-1,5-naphthylene |
| 1,7-heptylene | diphenyloxadiazole |
| 1,8-octylene | benzanilide |
| 2-methyl-1,3-propylene | diphenylurea |
| 2-methyl-2,4-pentylene | 1,2-bis(phenylcarbamyl)ethylene |
| 2,2-dimethyl-1,3-propylene | 1,4-bis-(phenylcarbamyl)butadiene |
| 1,5-hexylene | 1,2-bis-(phenylcarbamyl)ethane |
| 2,3-diphenyl-1,4-butylene | 1,3-bis-(phenylcarbamyl)propane |
| 1-carboxy-1,5-pentylene | —CH$_2$CH$_2$OCH$_2$CH— |
| 3-methyl-1,6-hexylene | —CH$_2$CH$_2$SCH$_2$CH$_2$— |
| vinylene | |
| propenylene | diphenyl |
| 1,3- or 1,4-phenylene | diphenyloxide |
| 3-sulpho-1,4-phenylene | diphenylamine |
| 4-sulpho-1,3-phenylene | diphenylsulphide |
| 2-carboxy-1,4-phenylene | diphenylsulphone |
| 4-carboxy-1,3-phenylene | diphenylmethane |
| 2-methoxy-1,4-phenylene | diphenylketone |
| diphenylethane | diphenylethylene |

 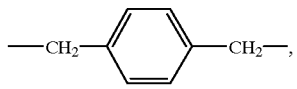

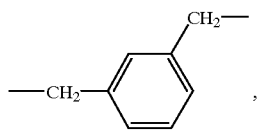 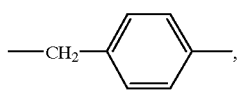

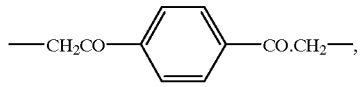 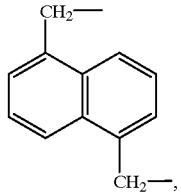

—(CH$_2$)$_2$NH(CH$_2$)NH(CH$_2$)$_2$—, —(CH$_2$)$_2$NH—(CH$_2$)$_2$—,

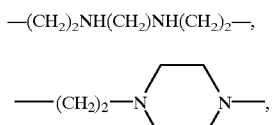 

 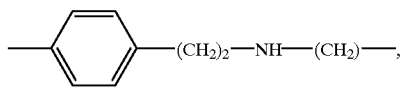

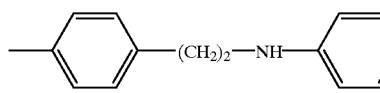 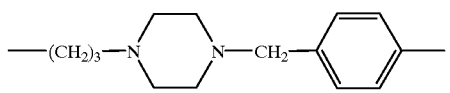

and

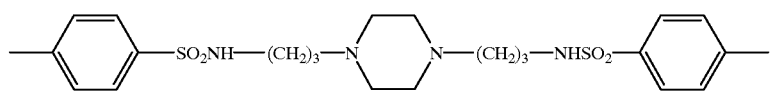

When the group —WLW$^1$— forms an optionally substituted piperazinylene group it is preferably of the Formula (12):

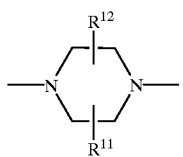

(12)

wherein:

R$^{11}$ and R$^{12}$ each independently is H, C$_{1-4}$-alkyl or substituted C$_{1-4}$-alkyl, more preferably H, C$_{1-4}$-alkyl or C$_{1-4}$-alkyl substituted by —OH, —COOH or —SO$_3$H and especially H, methyl, ethyl and hydroxyethyl.

Especially preferred piperazinylene groups represented by —WLW$^1$— include 1,4-piperazinylene, 2-methyl-1,4-piperazinylene, 2-hydroxyethyl-1,4-piperazinylene and 2,5-dimethyl-1,4-piperazinylene.

It is preferred that m is 0 or 1, more preferably 1.

In view of the hereinbefore mentioned preferences, a first preferred embodiment of the present invention is a compound of the Formula (13) and salts thereof:

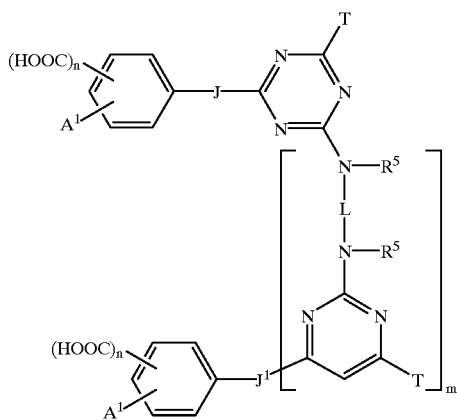

(13)

wherein:

J, J$^1$, m, n and each T, L and R$^5$ independently is as hereinbefore defined; and each A$^1$ independently is —SO$_3$H, —PO$_3$H$_2$, —OH, C$_{1-4}$-hydroxyalkyl, —C$_{1-4}$-alkoxy or hydroxy-C$_{1-4}$-alkoxy.

It is preferred that each A$^1$ independently is H, —PO$_3$H$_2$, —SO$_3$H or —OH, more preferably H.

It is especially preferred that each A$^1$ is H, n=2, m=0 or 1, and that the two phenyl groups shown at the left of Formula (13) are of the formula:

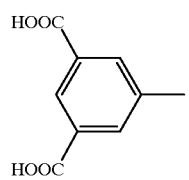

A second preferred embodiment of the present invention are compounds of Formula (13) wherein:

J and J$^1$ are each independently of the formula —NR$^1$—;

each T independently is —OR$^3$, —NR$^{14}$R$^{15}$, morpholine or piperazine;

R$^{13}$ and R$^{14}$ are each independently H, C$_{1-6}$-alkyl or C$_{1-6}$-alkyl substituted by —OH, —SO$_3$H or —COOH;

R$^{15}$ is H or C$_{1-4}$-alkyl;

m is 0 or 1; and

R$^1$ is H, C$_{1-4}$-alkyl or C$_{1-4}$-alkyl substituted by —OH, —SO$_3$H or —COOH.

It is to be understood that the present invention includes not only the compounds in their free acid form but also to the salts thereof and mixtures of compounds of Formula (1).

Preferred salts are those with an alkali metal, particularly Na$^+$, Li$^+$ or K$^+$, ammonium or a substituted ammonium cation.

The substituted ammonium cation may be a quaternary ammonium group of the formula $^+$NQ$_4$ in which each Q independently is an organic radical, or two or three Qs together with the nitrogen atom to which they are attached form a heterocyclic ring and all remaining Qs are selected from C$_{1-4}$-alkyl. Preferred organic radicals represented by Q are C$_{1-4}$-alkyl radicals, especially methyl. Preferred heterocyclic rings formed by $^+$NQ$_4$ are 5 or 6 membered heterocyclic rings.

As examples of quaternary ammonium groups of formula $^+$NQ$_4$ there may be mentioned N$^+$(CH$_3$)$_4$, N$^+$(CH$_3$)$_4$, N$^+$(CH$_2$CH$_3$)$_4$, N-methyl pyridinium, N,N-dimethyl piperidinium and N,N-dimethyl morpholinium.

Alternatively, the substituted ammonium cation may be a group of formula $^+$NHT$_3$ wherein each T independently is H or C$_{1-4}$-alkyl, or two or three groups represented by T together with the nitrogen atom to which they are attached form a 5 or 6 membered ring, especially a pyridine, piperidine or mopholine ring.

As examples of groups of formula $^+$NHT$_3$ there may be mentioned (CH$_3$)$_3$N$^+$H, (CH$_3$)$_2$N$^+$H$_2$, H$_2$N$^+$(CH$_3$)(CH$_2$CH$_3$), CH$_3$N$^+$H$_3$, CH$_3$CH$_2$N$^+$H$_3$)$_2$, CH$_3$CH$_2$CH$_2$N$^+$H$_3$, $^+$NH$_4$, (CH$_3$)$_2$CHN$^+$H$_3$, pyridinium, piperidinium and morpholinium.

According to a further feature of the present invention there is provided a process for the preparation of compounds of the Formula (1) wherein m is 1 or 2 comprising:

(1) condensing a compound of the formula Ar—J—H with a compound of the formula X$^2$Q$_2^1$, preferably in the presence of a base;

(2) condensing a compound of the formula Ar$^1$—J$^1$—H with a compound of the formula X$^2$Q$_2^1$, preferably in the presence of the base;

(3) condensing the product of step (1) with a compound of formula (14):

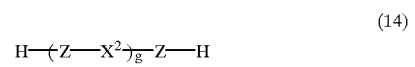

(14)

preferably in the presence of a base;

(4) condensing the product of stage (3) with the product of stage (2); and (5) when T is not a labile atom or group, condensing the compound from step (4) with a compound of the formula TH;

wherein:

each Q$^1$ independently is a labile atom or group;

Ar, Ar$^1$, J, J$^1$ and T are as hereinbefore defined;

g is 0 or 1;

each $X^2$ independently is as hereinbefore defined for X and $X^1$ except in place of substituent T in formulae (4), (5) and (6) there is $Q^1$, where $Q^1$ is hereinbefore defined; and each Z independently is a group of the formula —W—L—$W^1$— wherein W, L and $W^1$ independently are as hereinbefore defined.

Preferred labile atoms are halogens, especially Cl and Br and a preferred labile group is —$OSO_3H$. It is especially preferred that $Q_1$ is Cl.

When m=0 in Formula (1), the compounds may be prepared by condensing the product of step (1) above with a compound of the formula $Ar^1$—$J^1$—H, preferably in the presence of a base, followed by step (5) of the above process.

Alternatively, the compounds of the formula $X^2Q_2^1$ used in steps (1), (2) and (3) of the above process may be replaced by compounds of the formulae $XQ_2^1$ and $X^1Q_2^1$, where $Q^1$, X and $X^1$ are as hereinbefore defined, such that the compounds of Formula (1) are formed without performing step (5) of the above process.

When J is a group of the formula (2) or (3), the compounds of the formula Ar—J—H and $Ar^1$—$J^1$—H may be prepared by condensation of a compound of formula (15) or (16)

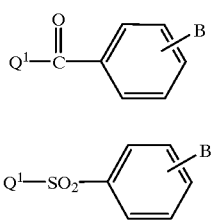

with a compound of the formula Ar—V—H wherein B is —OH, —SH, —$NR^1H$ or —$NO_2$; and $Q^1$, V, $R^1$ and Ar are as hereinbefore defined.

When B is a nitro group, it may be reduced to an —$NH_2$ group by any convenient means, for example by hydrogenation using palladium as a catalyst.

The base used in the condensation stages of the process may be any inorganic base such as an alkali metal or alkali earth metal hydroxide, carbonate or bicarbonate or an organic base. Preferred organic bases are tertiary amines such as N-alkylated heterocycles, for example N—($C_{1-4}$-alkyl)morpholine, N—($C_{1-4}$-alkyl)piperidine, N,N'-di($C_{1-4}$-alkyl)piperazine; tri($C_{1-4}$-alkyl)amines, for example triethylamine; and optionally substituted pyridines, especially pyridine.

The condensations are preferably performed in a liquid medium, preferably an aqueous medium and especially water. Ambient temperatures may be employed in conjunction with a reaction time of, for example, 5–24 hours, or elevated temperatures can be used for a shorter period.

After the condensations the product may be isolated by precipitating the product as a salt from the reaction mixture for example by the addition of a suitable alkali metal salt, especially sodium chloride. Alternatively, the product may be isolated in its free acid form by acidifying the reaction mixture, preferably using a mineral acid, especially hydrochloric acid. Where the product precipitates as a solid it may be separated from the mixture by filtration.

If desired unwanted anions may be removed from the product of the above process by dialysis osmosis, ultrafiltration or a combination thereof.

The product of the above process may be converted, where necessary, to the $NH_4^+$, quaternary ammonium or organic amine salt by the addition of ammonia, ammonium hydroxide, primary, secondary, tertiary or quaternary amine. When the base used in the condensation process is an organic amine an excess may be used so that the compound of Formula (1) is formed as the organic amine salt.

The compound of formula (14) where g is 1 may be prepared by:
 (a) condensing a compound of the formula HZH with a compound of the formula $X^2Q^1_2$; and
 (b) condensing the product from step (a) with a compound of the formula HZH;
wherein Z, $X^2$ and $Q^1$ are as hereinbefore defined.

Examples of compounds of formula Ar—J—H and $Ar^1$—$J^1$—H which may be used in the preparation of compounds of the Formula (1) include:

| | |
|---|---|
| 2-aminoisophthalic acid | 3-amino-4-fluorobenzoic acid |
| 4-aminoisophthalic acid | 3-amino-5-hydroxybenzoic acid |
| 5-aminoisophthalic acid | 3-amino-4-hydroxybenzoic acid |
| 3-aminophthalic acid | 3-amino-2-hydroxybenzoic acid |
| 4-aminophthalic acid | 2-amino-6-hydroxybenzoic acid |
| 2-aminoterephthalic acid | 2-amino-4-nitrobenzoic acid |
| 3-aminobenzoic acid | 3-amino-5-nitrobenzoic acid |
| 4-aminobenzoic acid | 2-nitro-3-aminobenzoic acid |
| anthranilic acid | 2-nitro-5-aminobenzoic acid |
| 4-sulphoanthranilic acid | 3-nitro-4-aminobenzoic acid |
| 5-sulphoanthranilic acid | 3-acetylamino-5-aminobenzoic acid |
| 2-amino-4-chlorobenzoic acid | 3-amino-4-methylbenzoic acid |
| 2-amino-5-chlorobenzoic acid | 2-amino-3-methylbenzoic acid |
| 3-amino-4-chlorobenzoic acid | 3-amino-4-methoxybenzoic acid |
| 5-amino-2-chlorobenzoic acid | 3-amino-4-hydroxybenzoic acid |
| 2-amino-5-methylbenzoic acid | 4-aminosalicylic acid |
| 2-amino-6-methylbenzoic acid | 5-aminosalicylic acid |
| 2-amino-5-bromobenzoic acid | 3-amino-2-naphthoic acid |
| 2-n-butoxy-4-aminobenzoic acid | 5-amino-2-naphthoic acid |
| 2-hydroxyisophthalic acid | mercaptobenzoic acid |
| 4-hydroxyisophthalic acid | 4-hydroxybenzoic acid |
| 5-hydroxyisophthalic acid | 3-hydroxybenzoic acid |
| 3-hydroxyisophthalic acid | salicylic acid |
| 2-hydroxyterephthalic acid | 5-mercaptoisophthalic acid |

The compound $X^2Q^1_2$ is preferably cyanuric chloride.

Suitable compounds of the formula H—W—L—$W^1$—H include for example piperazine, 2,5-dimethypiperazine, 2-, 3- and 4-aminobenzylamine, o-, m- and p-xylenediamines, o-, m-, p-phenylene diamine, meta-phenylenediamine sulphonic acid, metaphenylenediamine disulphonic acid, metaphenylenediamine carboxylic acid, metaphenylenediamine dicarboxylic acid and n-alkyldiamines, preferably ($C_{2-12}$)-n-alkyldiamines such as 1-8-diaminooctane.

Examples of compounds of the formula T—H suitable for the preparation of compounds of the Formula (1) include n-alkylamines such as n-hexylamine and n-octylamine, alkanolamines such as ethanol amine 1-propanolamine, diethanolamine, thiopropionic acid, thiopropionicacid, thiopropyl sulphonic acid, morpholine, 4-(2-hydroxyethyl) morpholine, piperidine and piperazine.

Examples of suitable compounds of the formula (15) and (16) include acid chlorides such as 4-aminobenzoyl chloride, 4-nitrobenzoyl chloride, 3-aminobenzoyl chloride, 4-aminobenzenesulphonyl chloride, 4-nitrobenzenesulphonyl chloride and 3-aminobenzenesulphonyl chloride.

The compounds of Formula (1) have been found to be useful as bleed reduction agents in inks. According to a second aspect of the present invention there is provided the use of a compound of Formula (1) as a bleed reduction agent.

The bleed reduction agents (BRA's) of Formula (1) exhibit high solubility in water and aqueous media and when incorporated in an ink result in prints which exhibit very low color to color and/or color to black bleed on a printed substrate.

A third aspect of the present invention provides an ink comprising a colorant, a liquid medium, preferably an aqueous medium, and a compound the Formula (1). It is preferred that the compound of Formula (1) is completely dissolved in the liquid medium to form a solution.

The ink preferably contains from 0.01 to 10 parts of a compound of Formula (1), more preferably 0.05 to 5 parts and especially from 0.1 to 0.5 parts based upon the weight of the ink. In embodiments the ink may contain more than one compound of the Formula (1), for example 2 or 3 such compounds.

The colorant is preferably a dye, more preferably a water soluble dye. Suitable dyes include, for example, azo, phthalocyanine, triphenodioxazine, formazan and anthraquinone dyes, especially water-soluble azo and phthalocyanine dyes. Preferred azo dyes are monoazo, disazo and trisazo dyes, especially those containing carboxy groups. Numerous suitable dyes are listed in the Colour Index International, for example direct dyes, acid dyes, food dyes, basic dyes, reactive dyes and disperse dyes. Specific examples of suitable dyes listed in the Colour Index International include Reactive Orange 12, Reactive Orange 13, Reactive Red 3:1, Reactive Red 31, Reactive Red 180, Reactive Blue 71, Reactive Black 31, Reactive Black 8, Reactive Yellow 85, Direct Yellow 86, Direct Yellow 132, Direct Blue 199, Direct Violet 106, Direct Black 168, Acid Red 249, Acid Red 52 and Acid Blue 9. Further suitable dyes include for example, Projet Fast Black 2, Food Black 2, Projet Fast Yellow 2, Projet Fast Cyan 2 and Projet Fast Magenta 2 (all of the Projet dyes are commercially available from Zeneca Limited).

Further specific suitable dyes include, for example, the dyes of formulae (17) to (27):

A dye of the Formula (17) and salts and mixtures thereof, especially ammonium salts:

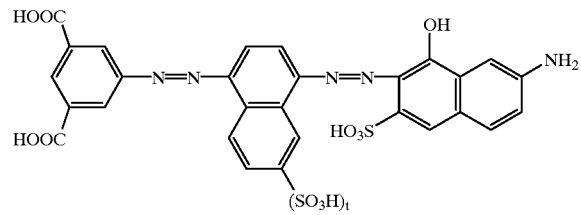

Formula (17)

wherein the t is 0 or 1.

The compounds of Formula (17) may be prepared using methods analogous to those described in the art for similar disazo compounds. For example, as described in Examples 1 and 2 of E 356 080.

A dye of the Formula (18) and salts thereof, especially ammonium salts:

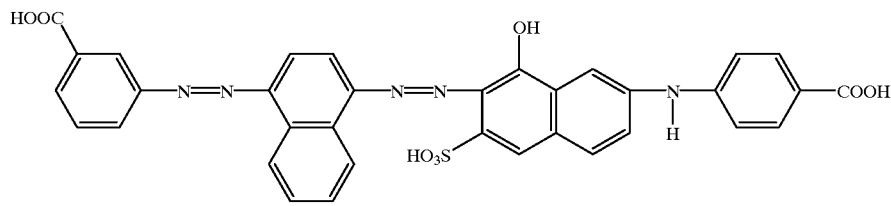

Formula (18)

the dye of Formula (18) may be prepared using methods analogous to those described in the art for other similar disazo compounds. For example as described in Example 1 of EP 572 419.

A dye of Formula (19) or salts thereof, especially ammonium salts;

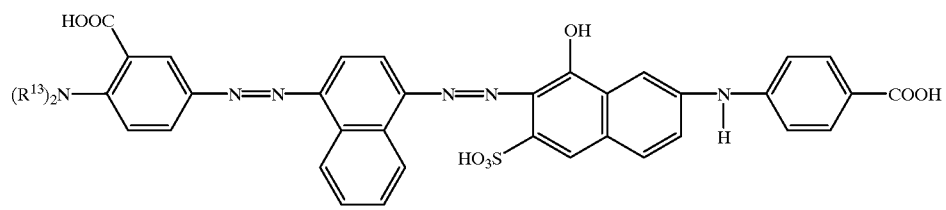

Formula (19)

wherein each $R^{13}$ independently is ethyl, propyl or butyl.

The dyes of Formula (19) may be prepared using methods analogous to those described in the art for other similar azo compounds. For example, an analogous process to that described in Example 1 EP 572 419, wherein in place of the 3-aminonobenzoic acid there is used 3-amino-2-(N,N-diethyl amino)benzoic acid, 3-amino-2-(N,N-propylamino) benzene acid or 3-amino-2-(N,N-dibutylamino)benzoic acid in stage 1.

Dyes of the Formula (20) or salt thereof:

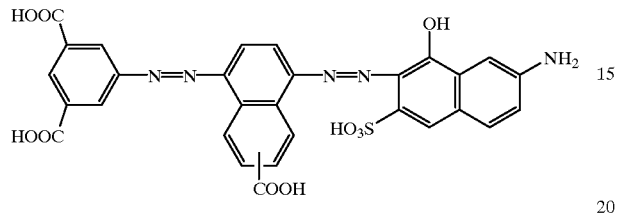

Formula (20)

The dyes of Formula (20) may, for example, be prepared as a mixture using the process in Example 8 of EP 356 080.

A dye of the Formula (21) and salts thereof:

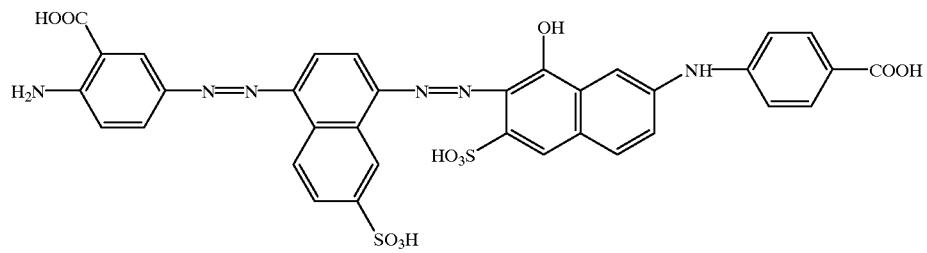

Formula (21)

The dye of Formula (21) may, for example, be prepared using an analogous process to that described in Example 4 of EP 572 419 wherein in place of 3-aminobenzoic acid in stage 1 there is used 3-amino-2-nitrobenzoic acid and following stage 3, the nitro group is reduced to amino by hydrogenation over a suitable catalyst.

Dyes of the Formula (22) and salts thereof:

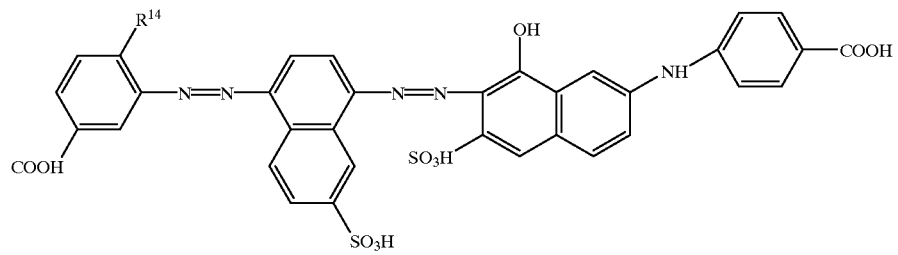

Formula (22)

wherein $R^{14}$ is H or —$CH_3$;

The dyes of Formula (22) may, for example, be prepared using the process described in Example 4 of EP 572 419, wherein when $R^{14}$ is —$CH_3$ in Formula (22) there is used 3-amino-4-methylbenzoic acid in place of 3-aminobenzoic acid in stage 1.

Dyes of the Formula (23) and salts thereof, especially ammonium salts;

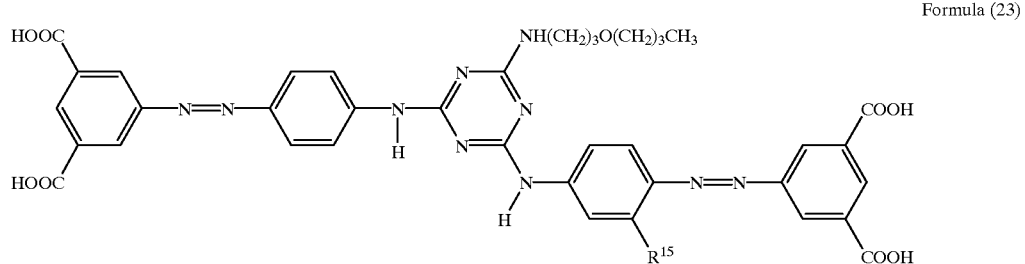
Formula (23)
wherein: $R^{15}$ is H or methyl;
the dyes of Formula (23) may be prepared by methods analogous to the Examples of EP 468 647;
A dye of Formula (24) or salts thereof:
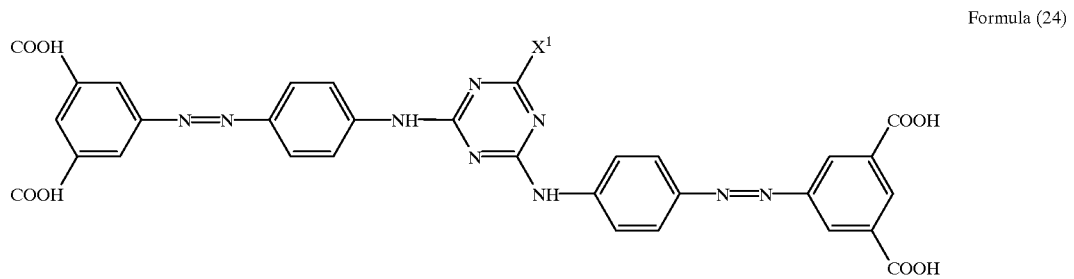
Formula (24)
wherein
$X^1$ is morpholinyl or —$NHR^{16}$; and
$R^1$ is n-hexyl.
The dye of Formula (24) may be prepared using the process described in Example 10 and 15 of EP 468 647A.
A dye of the formula (25) and salts thereof:
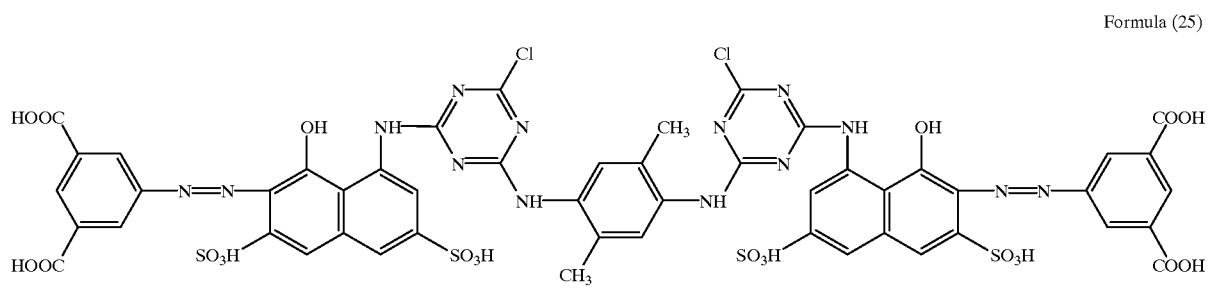
Formula (25)

the dye of Formula (25) may be prepared using a method analogous to Example 1 of EP 468 648, wherein in place of phenylenediamine there is used 2,5-dimethyl-1,4-phenylene diamine.

A dye of the Formula (26) and salts thereof:

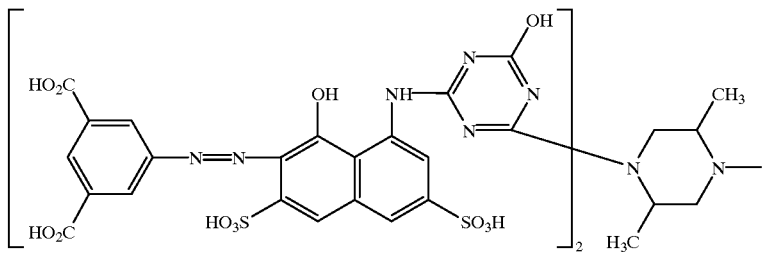

(Formula 26)

The dye of Formula (28) may be prepared using the method described in Example 3 of EP 679 173 B1;

A dye of the Formula (7) and salts thereof:

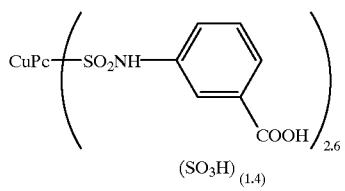

Formula (27)

wherein CuPc is a copper phthalocyanine nucleus.

The dye of Formula (27) may be prepared as described in Example 3 of EP 559 309 A2.

The ink may contain a single colorant or a mixture of colorants.

The colorant is preferably present in the ink at a concentration of 0.5 to 20 parts, more preferably from 1 to 15 parts and especially from 1 to 5 parts by weight based upon the weight of the ink.

The liquid medium is preferably water or a mixture of water and one or more water-soluble organic solvent. The weight ratio of water to organic solvent(s) is preferably from 99:1 to 1:99, more preferably from 95:1 to 50:50 and especially from 90:10 to 60:40.

The water-soluble organic solvent is preferably selected from $C_{1-4}$-alkanols such as methanol, ethanol, n-propanol, isopropanol, n-butanol, sec-butanol, tert-butanol or isobutanol; amides such as dimethylformamide or dimethylacetamide; ketones or ketone-alcohols such as acetone or diacetone alcohol; ethers such as tetrahydrofuran or dioxane; oligo- or poly-alkylene glycols such as diethylene glycol, triethylene glycol, polyethylene glycol or polypropylene glycol; alkenyleneglycols or thioglycols containing a $C_2$-$C_6$-alkylene group such as ethylene glycol, propylene glycol, butylene glycol, pentylene glycol or hexylene glycol, thioglycol and thiodiglycol; polyols such as glycerol or 1,2,6-hexanetriol; $C_{1-4}$-alkyl-ethers of polyhydric alcohols such as 2-methoxyethanol, 2-(2-methoxyethoxy)ethanol, 2-(2-ethoxyethoxy)-ethanol, 2-[2-(2-methoxyethoxy) ethoxy]ethanol, 2-[2-(2-ethoxyethoxy)-ethoxy]-ethanol; heterocyclic ketones, such as 2-pyrrolidone and N-methyl-2-pyrrolidone; or mixtures containing two or more of the aforementioned water-soluble organic solvents for example thiodiglycol and a second glycol or diethylene glycol and 2-pyrrolidone.

Preferred water-soluble organic solvents are 2-pyrrolidone; N-methylpyrrolidone; alkylene glycols and oligo-alkylene glycols, such as ethylene glycol, diethylene glycol, triethylene glycol; and lower alkyl ethers of polyhydric alcohols such as 2-methoxy-2-ethoxy-2-ethoxy-ethanol; polyethylene glycols with a molecular weight of up to 500; and thioglycols such as thiodiglycol. A preferred specific solvent mixture is a binary or ternary mixture of water and diethylene glycol and/or, 2-pyrrolidone or N-methylpyrrolidone in weight ratios 75–90:25–5 and 60–96:2–20:2–20 respectively. An especially preferred specific solvent mixture is a binary or tertiary mixture of water and thiodiglycol and/or 2-pyrrolidone or N-methylpyrrolidone in weight ratios 75–98:25–2 and 80–96:2–10:2–10 respectively.

The inks may also contain other additives, for example, viscosity and surface tension modifiers and one or more surfactants to aid the penetration of the colorant into the substrate used for printing. Suitable surfactants include anionic surfactants for example, fatty acid salts and alkylbenzenesulphonates; cationic surfactants for example, aliphatic amine salts and quaternary ammonium salts; and non-ionic surfactants for example, ethylene oxide adducts of higher alcohols, of alkylphenols, of higher alcohol fatty acid esters, of fatty acid amides, of polypropylene glycol, of acetylene, fatty acid esters of polyhydric alcohols and amino acid and betaine type amphoteric surfactants. It is preferred that the surfactant is a non ionic surfactant, for example SURFYNOL 465™ (available from Air Products Ltd). When a surfactant is used in the ink, it is preferably present at a concentration in the range of from 0 to 10 parts, more preferably at from 0 to 5 parts by weight based upon the weight of the ink.

Acids or bases may be present in the ink to adjust the pH of the ink, for example ammonia solution. A buffer may also be present to stabilise the pH of the ink. Any convenient buffer may be used including phosphates, for example $Na_2HPO_3$, borates, for example sodium borate and EDTA.

Where the inks are used in thermal ink jet printing processes, the ink may also contain a kogation reducing agent to prevent or reduce the build up of residue on the surface of the rotor used to heat the ink in the ink jet head.

The kogation-reducing agent is preferably an oxo anion, such as described in EP 425150A. The oxo-anion may be $C_2O_4^{2-}$, $SO_3^{2-}$, $SO_4^{2-}$—, molybdate, $AsO_4^{3-}$ or more preferably a phosphate ester, a diorganophosphate or more especially a phosphate salt which is particularly effective in reducing kogation. As examples of phosphate salts there may be mentioned dibasic phosphate ($HPO_4^{2-}$) monobasic phosphates ($H_2PO_4-$) and polyphosphates ($P_2O_7^{4-}$). The selection of counter ion is not believed to be critical and examples include alkali metals, ammonium and alkylammonium cations.

The kogation-reducing agent is preferably present in the ink at a concentration from 0.001% to 15%, based on oxo-anion, and more preferably from 0.01% to 1% (by weight).

Further examples of suitable ink media are given in U.S. Pat. No. 4,963,189, U.S. Pat. No. 4,703,113, U.S. Pat. No. 4,626,284, EP-A425,150 and U.S. Pat. No. 5,207,824 which are incorporated herein by reference thereto.

In view of the forgoing preferences a particularly preferred ink comprises:
- (a) from 0.01 to 10 parts, more preferably 0.1 to 5 parts of a compound of Formula (1);
- (b) from 0.5 to 20 parts of a water-soluble dye;
- (c) from 50 to 98 parts water; and
- (d) from 2 to 50 parts of water-soluble organic solvent(s);
wherein the parts (a), (b), (c) and (d) are parts by weight and the sum of the parts (a)+(b)+(c)+(d)=100.

The pH of the ink according to the third aspect of the present invention is preferably from 7 to 10, more preferably from 8 to 9.

It is preferred that when the compounds of formula (1) are added to an ink that they do not markedly affect the color of the ink. Accordingly, it is preferred that the compounds of Formula (1) are colorless, or substantially colorless, especially when they are used in colored inks.

A fourth aspect of the present invention provides a process for printing a substrate with an ink using an ink jet printer, characterised in that the ink contains at least one compound of Formula (1).

Preferred inks are those according to the third aspect of the present invention.

A suitable process for the application of an ink as hereinbefore defined comprises forming the ink into small droplets by ejection from a reservoir through a small orifice so that the droplets of ink are directed at a substrate. This process is commonly referred to as ink jet printing, and preferred ink jet printing processes for the present inks are piezoelectric ink jet printing and thermal ink jet printing. In thermal ink jet printing, droplets of ink are ejected from an ink jet nozzle during relative movement between the nozzle and the substrate in response to an electrical recording signal which heats a resistor in the ink jet head thereby heating the ink and causing ejection of ink droplets from the nozzle.

Suitable substrates include plastic, textile, metal, glass, ceramics, overhead projector slides and paper, especially paper and a textile material.

Preferred papers include plain and treated papers, which may have an acid, alkaline or neutral character, for example Xerox Acid 4024 Paper, Xerox Alkaline paper (both available from Xerox Inc.), Wiggins, Conqueror (Available from Wiggins Teape Ltd in the UK), Gilbert Bond Paper, Hewlett Packard coated papers such as HP 516347, HP Premium Coated Paper and HP Photopaper, Stylus Pro 720 dpi Coated Paper, Epson Photo Quality Glossy Film (available from Seiko Epson Corp.), Epson Photo Quality Glossy Paper (available from Seiko Epson Corp.) Canon HR 101 High Resolution Paper (available from Canon), Canon GP 201 Glossy Paper (available from Canon), and Canon HG 101 High Gloss Film (available from Canon).

Preferred textile materials include a natural, semi-synthetic or synthetic material. Examples of natural textile materials include wool, silk, hair and cellulosic materials, particularly cotton, jute, hemp, flex and linen. Examples of synthetic and semi-synthetic materials include polyamides, polyesters, polyacrylonitriles and polyurethanes.

An especially preferred substrate is paper, especially plain paper which may have an acid, basic or neutral character.

According to a fifth aspect of the present invention there is provided a paper, a textile material, a metal, ceramic or glass substrate printed with an ink according to the third aspect of the present invention.

A Sixth aspect of the present invention provides an ink jet printer cartridge containing an ink according to the second aspect of the present invention.

The invention is further illustrated but not limited by the following examples.

EXAMPLE 1

Of Bleed Reduction Agent 1 (BRA 1)

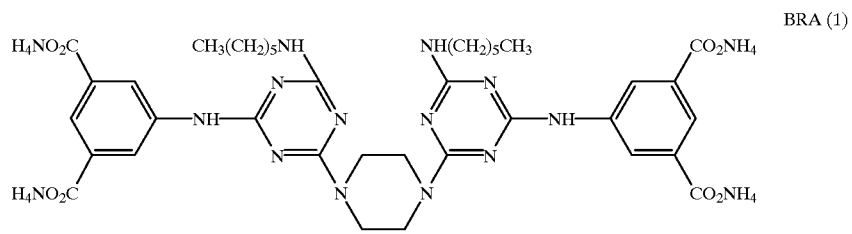

BRA (1)

BRA (1) was prepared as follows:
(a) Preparation of:

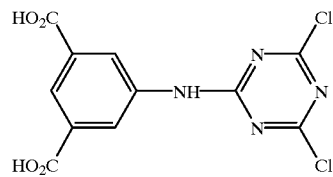

5-aminoisophthalic acid (90.5 g) was dissolved in water (1 l) by addition of dilute sodium hydroxide solution to pH7. Cyanuric chloride (96.8 g) was dissolved in acetone (400 ml) and water (400 ml) and the solution cooled to 0–5° C. The above aminoisophthalic acid solution was added dropwise at 0–5° C. and stirred at this temperature for 2 hours maintaining the pH at 7–7.5.

The product was filtered off and dried under vacuum at 30° C. over calcium chloride.

(b) Condensation with Piperazine

The product from stage (a) (48.3 g) was added to a mixture of water (250 ml) and acetone (250 ml) and the pH adjusted to 7 using 2N NaOH solution. Piperazine hexahydrate (7.8 g) was dissolved in water (100 ml) and the pH adjusted to 7 by addition of dilute hydrochloric acid. This solution was then added to the above dichlorotriazinylamino-isophthalic acid solution and stirred for 18 hours at 20–25° C. maintaining the pH at 7–8. The volume was adjusted to 1500 ml by addition of water.

(c) Condensation with n-hexylamine n-Hexylamine (45.5 g) was added to the product of stage (b) and the temperature raised to 70–80° C. It was stirred at this temperature for 2 hours. After cooling to 20° C. the pH was adjusted to 6 with 2N hydrochloric acid and the product was isolated by filtration.

The product was dissolved in water by addition of ammonium hydroxide solution to pH 9–9.5 and the solution dialysed until chloride ions could no longer be detected. The title product was then isolated by evaporating the reaction mixture followed by drying under vacuum at 50° C.

EXAMPLE 2

Bleed Reduction in Agent BRA (2) The Ammonium Salt of:

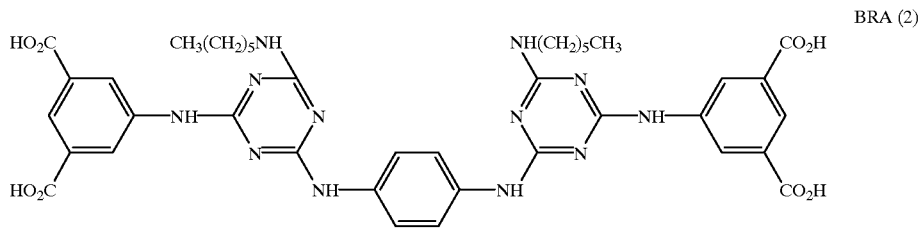

BRA (2) was prepared as in Example 1 except in place of the piperazine hexahydrate used in Example 1 there was used 1,4-phenylene diamine (4.3 g).

EXAMPLE 3

BRA (3) The Ammonium Salt of:

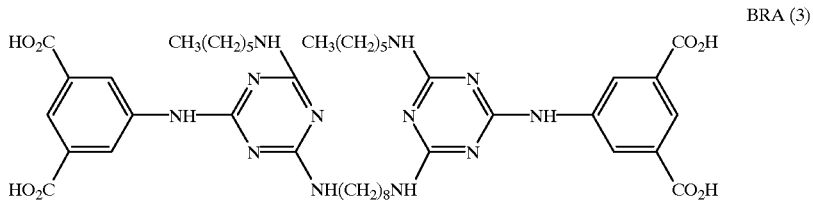

BRA (3) was prepared as in Example 1 except in place of the piperazine hexahydrate used in Example 1 there was used of 1,8-diaminooctane (5.8 g).

EXAMPLE 4

Preparation of BRA (4): The Ammonium Salt of:

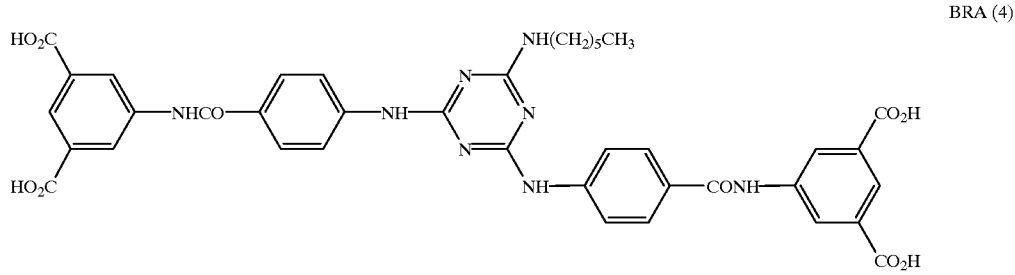

BRA (4) was prepared as follows:
(a) Preparation of:

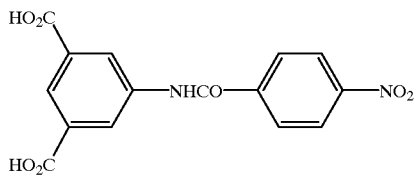

5-Aminoisophthalic acid (36.2 g) was dissolved in N,N-dimethylacetamide (200 ml) at 40° C. and a solution of 4-nitrobenzoyl chloride (37.1 g) in toluene (200 ml) added over 5 minutes at 40–50° C. The temperature was then raised to 60° C. to complete the reaction and the mixture cooled to 20° C. A mixture of ethanol (100 ml) and water (500 ml) was added and the precipitated product filtered and washed with water. The product was dried at 60° C., to give a yield of 68 g.

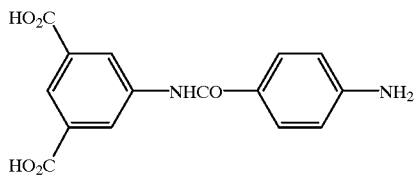

Stage (b)

The nitro compound (67 g) from stage (a) was dissolved in a mixture of water (750 ml) and ethanol (750 ml) by adjusting the pH to 7.0 with 2N sodium hydroxide solution. The solution was screened using a carbon filter and then hydrogenated at room temperature and atmospheric pressure over a palladium/carbon catalyst.

The solution was screened to remove the catalyst and acidified to pH5 with 2N hydrochloric acid. The precipitated product was filtered washed with water (500 ml) and dried at 60° C. Yield 52 g.

Stage (c)

The product of stage (b) (7.5 g) was dissolved in water (500 ml) by addition of 2N sodium hydroxide solution to pH7. The solution was cooled to 0–10° C.

Cyanuric chloride (5.0 g) was dissolved in acetone (50 ml) and the solution added slowly to the above amine solution at 0–10° C. The mixture was stirred for 2 hours at 0–10° C. maintaining the pH at 6–7 with 2N solution hydroxide addition.

A second solution of the product of stage (b) (7.5 g) in water (500 ml) at pH7 was added to the above solution and the mixture stirred for 18 hours at 20–25° C. and pH 6–7. The monochlorotriazinyl derivative precipitate was filtered, re-dissolved in water (800 ml) and salted to 10% with sodium chloride. The product was isolated by filtration and washed with 15% sodium chloride solution.

(d) Condensation with n-hexylamine

The product from stage (c) was added to water (800 ml) and n-hexylamine (15 g) added. The mixture was stirred and heated at 70–80° C. for 3 hours, salted to 10% with sodium chloride. The sodium salt of the title product was filtered off and washed with 15% sodium chloride solution.

The product was converted to its ammonium salt by dissolving in water (800 ml) and adjusting the pH to 9 with concentrated ammonium hydroxide solution. The solution was added to 1N hydrochloric acid and the title product in free acid form filtered off. The above procedure was repeated and then dissolved in dilute ammonium hydroxide solution at pH 9–10. The solution was dialysed until chloride ions could not be detected, the solution was then screened through a 0.45 μm nylon filter, evaporated and dried at 70° C. to give the title product.

EXAMPLE 5

Preparation of BRA (5) The Ammonium Salt of:

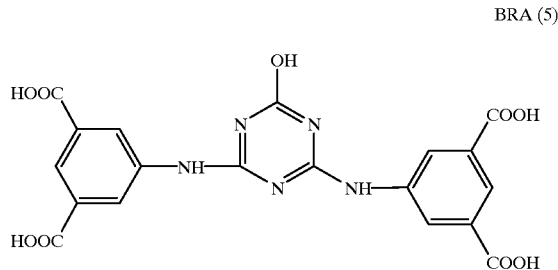

BRA (5)

(a) Preparation of 2,4-bis(3,5 dicarboxyphenylamino)-6-chloro triazine 5-aminoisophthalic acid (36.2 g) was dissolved in water (300 mls) by addition of sodium carbonate to pH7. Cyanuric chloride (18.4 g) was dissolved in acetone (100 mls) and water (100 mls) and the solution cooled to 0–5° C. The 5-aminoisophthalic solution was then added dropwise at 0–5° C. and stirred for 2 hours maintaining pH 6–7. The temperature was then increased to room temperature and the solution stirred for a further 12 hours at pH 7–8. The monochlorotriazine derivative was filtered off and dried under vacuum over calcium chloride at 60° C.

(b) Hydrolysis of the monochlorotriazine compound

The product from stage (a) (23.7 g) was added to water (200 mls) and pH adjusted to 11 using 2N sodium hydroxide. 1,4-diazabicyclo(2.2.2)octane (5.6 g) was dissolved in water (50 mls) and added to the above solution. This mixture was stirred for 2 hours at 80–90° C. maintaining pH at 11. After cooling to room temperature the pH was adjusted to 6 with 2N HCl and the title product was isolated by filtration.

The product was then converted to the ammonium salt by dissolving in water by addition of ammonium hydroxide solution to pH 9–9.5 and the solution dialysed until chloride ions could no longer be detected. The title product was isolated by evaporation followed by drying under vacuum at 50° C.

EXAMPLES 6 to 10

Inks

In examples 6 to 10 yellow and black inks were prepared according to the formulations shown in Table 1 in which the figures denote parts by weight for each stated component.

TABLE 1

| Ink | Colorant | Colorant Content | BRA | BRA Content | DEG | H$_2$O | Ink Colour |
|---|---|---|---|---|---|---|---|
| A | Projet Fast Black 2 | 2.5 | BRA (1) | 0.25 | 8 | 89.25 | Black |
| B | Projet Fast Black 2 | 2.5 | BRA (2) | 0.25 | 8 | 89.25 | Black |
| C | Projet Fast Black 2 | 2.5 | BRA (3) | 0.25 | 8 | 89.25 | Black |
| D | Projet Fast Black 2 | 2.5 | BRA (4) | 0.25 | 8 | 89.25 | Black |
| E | Projet Fast Black 2 | 2.5 | BRA (5) | 0.25 | 8 | 89.25 | Black |

TABLE 1-continued

| Ink | Colorant | Colorant Content | BRA | BRA Content | DEG | H$_2$O | Ink Colour |
|---|---|---|---|---|---|---|---|
| F | Projet Fast Yellow 2 | 2.5 | BRA (1) | 0.25 | 8 | 89.25 | Yellow |
| G | Projet Fast Yellow 2 | 2.5 | BRA (2) | 0.25 | 8 | 89.25 | Yellow |
| H | Projet Fast Yellow 2 | 2.5 | BRA (3) | 0.25 | 8 | 89.25 | Yellow |
| I | Projet Fast Yellow 2 | 2.5 | BRA (4) | 0.25 | 8 | 89.25 | Yellow |
| J | Projet Fast Yellow 2 | 2.5 | BRA (5) | 0.25 | 8 | 89.25 | Yellow |

In Table 1:
BRA = Bleed reduction agent of Formula (1), as defined in Examples 1 to 5;
DEG = Diethylene glycol,
Projet Fast Black 2 and Project Fast Yellow 2 are available from Zeneca Limited.

Bleed Assessment

A black ink and a yellow ink selected from Table 1 were printed onto plain paper (Xerox™ Acid 4024 and Gilbert Bond™) using a Hewlett Packard HP 500C ink jet printer as a series of vertical and horizontal bars of black ink intermixed with yellow ink.

The colour to colour bleed of a black ink bar into an adjacent yellow ink bar was assessed after allowing the prints to dry by measuring the degree of colour migration from one coloured bar to another using the scale shown in Table 2.

TABLE 2

| Colour to colour migration ($\mu$m) | <100 | 100–300 | 301–500 | 501–2400 | >2400 |
|---|---|---|---|---|---|
| Scale reference | 5 (None) | 4 (Negligible) | 3 (Slight) | 2 (Moderate) | 1 (Heavy) |

The results of the colour bleed tests are shown in Table 3.

TABLE 3 colour bleed between black and yellow inks containing BRA's

| Example | Black Ink | Yellow Ink | Colour to colour bleed scale reference |
|---|---|---|---|
| 6 | A | F | 5 (none) |
| 7 | B | G | 5 (none) |
| 8 | C | H | 5 (none) |
| 9 | D | I | 4 (negligible) |
| 10 | E | J | 4 (negligible) |

COMPARATIVE EXAMPLE (i)

A black ink and a yellow ink were prepared as in Table 1 without using a BRA (i.e. no compound of Formula (1) present in the ink), the 0.25% balance in the inks being water.

When the inks without BRA's were printed in the same pattern as that used in Examples 6 to 10 the bleed between the adjacent black and yellow bars was 2 (moderate) using the scale reference of Table 2.

EXAMPLE 11

The following ink formulations were prepared:

| Yellow ink: | |
|---|---|
| Projet Fast Yellow 2 | 2 parts |
| DEG | 8 parts |
| Bleed Reduction Agent: Example 1 | 0.2 parts |
| H$_2$O | 89.8 parts |
| Cyan ink: | |
| Projet Fast Cyan 2 | 2 parts |
| DEG | 8 parts |
| Bleed Reduction Agent: Example 1 | 0.2 parts |
| H$_2$O | 89.8 parts |
| Magenta ink: | |
| Projet Fast Magenta 2 | 2 parts |
| DEG | 8 parts |
| Bleed Reduction Agent: Example 1 | 0.2 parts |
| H$_2$O | 89.8 parts |

DEG=Diethylene glycol

Projet Fast Yellow 2, Projet Fast Cyan 2 and Projet Fast Magenta 2 are available from Zeneca Limited.

The three inks were loaded into a three colour cartridge and ink jet printed as in Examples 6 to 10 as a series of vertical and horizontal bars of the inks and ink mixtures shown in (a) of (f) below to give a coloured 'tartan' pattern:

(a) Cyan
(b) Yellow and Magenta
(c) Yellow
(d) Yellow and Cyan
(e) Magenta and Cyan
(f) Magenta On assessing the colour to colour bleed of adjacent differently coloured bars using the scale in Table 2, the overall bleed between the colours (a) to (f) above was 4 (negligible).

EXAMPLE 12

The inks described in Table 4 may be prepared according to the formulations shown. Numbers quoted in the fourth column onwards refer to the number of parts of the relevant ingredient and all parts are by weight. The column headed BRA are the BRA's prepared in Examples 1 to 5 above. The numbers in the second column refer to the number of parts by weight of the dye in the first column.

The inks may be applied to paper by thermal or piezo ink jet printing.

The following abbreviations are used in Table 4:
PG=propylene glycol
DEG=diethylene glycol
NMP=N-methyl pyrollidone
CAR=butylcarbitol
GLY=glycerol
2P=2-pyrollidone
P12=propane-1,2-diol
PHO=Na$_2$HPO$_4$ and
TDG=thiodiglycol
PEG=polyethylene glycol
5P=Pentane-1,5-diol
EG=ethylene glycol
H$_2$O=water
TEA=triethanolamine In Table 4 under the column marked "dye"
Dye 1 is Projet Fast Black 2;
Dye 2 is Projet Fast Yellow 2;
Dye 3 is Projet Fast Cyan 2;
Dye 4 is Projet Fast Magenta 2;
all of the above dyes are available from Zeneca Limited.

V and $V^1$ are each, independently, —O—, —S— or —$NR^1$—;

X and $X^1$ are each, independently, a group of the Formula (4), (5) or (6):

TABLE 4

| Dye | Dye content | BRA | BRA content | H₂O | PEG | 5P | EG | TEA | GLY | NMP | TDG | PHO | P12 | CAR | DEG |
|---|---|---|---|---|---|---|---|---|---|---|---|---|---|---|---|
| 1 | 5 | 1 | 0.5 | 49.5 | 10 | 4 | | | | | | 1 | | | 30 |
| 2 | 3.5 | 1 | 0.3 | 63.2 | | | 10 | 3 | 20 | | | | | | |
| 3 | 4 | 3 | 0.8 | 72.2 | | 5 | | | | | | | | | 18 |
| 4 | 6 | 5 | 0.6 | 80.4 | | | | 4 | | 9 | | | | | |
| 3 | 10 | 4 | 1.3 | 67.7 | | | | 2 | | 9 | 9 | 1 | | | |
| 2 | 3 | 2 | 0.6 | 77.4 | 10 | 5 | | | | 4 | | | | | |
| 2 | 6 | 3 | 0.5 | 58.5 | | 5 | | | | | | | | | 30 |
| 1 | 3 | 5 | 0.6 | 67.4 | | | | 1 | 15 | 10 | | 3 | | | |
| 3 | 3.5 | 1 | 0.7 | 26.2 | | 12 | | | | 10 | | | | | |
| 2 | 5 | 2 | 0.5 | 50.5 | | 10 | | 4 | 30 | | | | | | |
| 4 | 10 | 4 | 2 | 67 | 2 | 9 | 9 | | | | 1 | | | | |
| 4 | 6 | 3 | 1.2 | 57.8 | | | | 5 | | 15 | | | 2 | 13 | |
| 1 | 3 | 5 | 0.6 | 61.4 | | | 5 | | 20 | 10 | | | | | |
| 3 | 4 | 2 | 0.4 | 72.6 | | | | 5 | 9 | 9 | | | | | |
| 2 | 3.5 | 1 | 0.7 | 73.8 | 6 | 6 | | 5 | 5 | | | | | | |
| 3 | 4 | 3 | 0.5 | 81.5 | 1 | | | 10 | | | | 3 | | | |
| 4 | 2 | 5 | 0.3 | 65.7 | | | | | | | | | | 30 | 2 |
| 3 | 2 | 2 | 0.35 | 45.65 | | | | | | | | | | 20 | 32 |

What is claimed is:

1. An ink comprising a colorant, a liquid medium and a compound of formula 1 or a salt thereof:

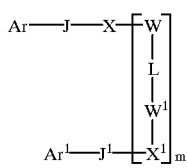

(1)

wherein:

Ar and $Ar^1$ are each, independently, an optionally substituted aromatic group and at least one of Ar and $Ar^1$ carries at least one group selected from —COOH and —$PO_3H_2$;

J and $J^1$ are each, independently, —O—, —S—, —$NR^1$— or a group of the Formula (2) or (3):

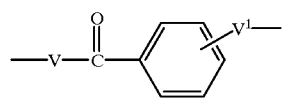

(2)

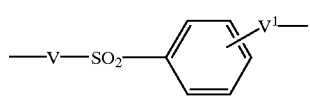

(3)

V and $V^1$ are each, independently, —O—, —S— or —$NR^1$—;

X and $X^1$ are each, independently, a group of the Formula (4), (5) or (6):

(4)

(5)

(6)

T is —$OR^2$, —$SR^2$, —$NR^3R^4$, a halogen atom, a thiocyano group or a quaternary ammonium group;
Y is H, CN or T;
E is Cl or CN;
each $R^1$ is, independently, H or optionally substituted alkyl;
$R^2$, $R^3$ and $R^4$ are each, independently, H, alkenyl, substituted alkenyl, alkyl, substituted alkyl, aryl, substituted aryl, aralkyl, substituted aralkyl, cycloalkyl or substituted cycloalkyl, or $R^3$ and $R^4$ together with the nitrogen atom to which they are attached form a 5 or 6 membered ring;
W and $W^1$ are each, independently, —O—, —S—, or —$NR^5$— or optionally substituted piperazinylene;
$R^5$ is H or optionally substituted alkyl;
L is a divalent organic linking group; or the group —WLW$^1$— forms an optionally substituted piperazinylene group; and m is 0, 1 or 2.

2. An ink according to claim 1 wherein at least one of Ar and Ar$^1$ carries at least one —COOH group.

3. An ink according to claim 1 wherein both Ar and Ar$^1$ carries at least one —COOH group.

4. An ink according to claim 1 wherein Ar and Ar$^1$ each independently is a group of the formula (7):

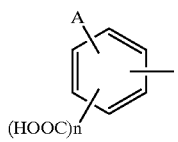

(7)

wherein:

n is 1 or 2;

A is H, alkyl, substituted alkyl, alkoxy, substituted alkoxy, halogen, —SO$_3$H, —PO$_3$H$_2$, OR$^6$ or —NR$^6$R$^7$; and R$^6$ and R$^7$ are each independently H, C$_{1-4}$-alkyl, phenyl, or R$^6$ and R$^7$ together with the nitrogen to which they are attached form a 5 or 6 membered ring.

5. An ink according to claim 4 wherein A is selected from H, C$_{1-4}$-alkyl, C$_{1-4}$-hydroxyalkyl, —SO$_3$H, —PO$_3$H$_2$, —OH, —Cl, C$_{1-4}$-alkoxy and hydroxy —C$_{1-4}$-alkoxy.

6. An ink according to claim 1 wherein:

J, J$^1$, m, n, and each T, L and R$^5$ independently is as defined in claim 1; and each A$^1$ independently is —SO$_3$H, —PO$_3$H$_2$, —OH, —Cl, C$_{1-4}$-alkoxy and hydroxy —C$_{1-4}$-alkoxy.

7. An ink according to claim 1 wherein m is 0 or 1.

8. A compound according to claim 1 wherein each A$^1$ is H, n=2, m=0 or 1, and Ar and Ar$^1$ are of the formula:

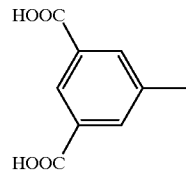

9. A compound according to claim 1 wherein T is —OR$^2$, —SR$^2$ or NR$^2$R$^3$ wherein R$^2$ and R$^3$ are as defined in claim 1.

10. A compound according to claim 1 wherein:

J, J$^1$ are each of the formula —NR$^1$—;

each T independently is —OR$^{13}$, NR$^{14}$R$^{15}$, morpholine or piperazine;

R$^{13}$ and R$^{14}$ are each independently H, C$_{1-6}$ alkyl or C$_{1-6}$ alkyl substituted by —OH, SO$_3$H or —COOH;

R$^{15}$ is H or C$_{1-4}$ alkyl;

M is 0 or 1; and

R$^1$ is H, C$_{1-4}$ alkyl or C$_{1-4}$ alkyl substituted by —OH, —SO$_3$H or COOH.

11. An ink according to claim 1 in the form of an ammonium or substituted ammonium salt.

12. An ink according to claim 1 comprising:

(a) from 0.01 to 10 parts of a compound of formula (1);

(b) from 0.5 to 20 parts of a water-soluble dye;

(c) from 50 to 98 parts water; and (d) from 2 to 50 parts of water-soluble organic solvent(s);

wherein the parts (a), (b), (c) and (d) are parts by weight and the sum of the parts (a)+(b)+(c)+(d)=100.

13. An ink according to claim 1 wherein the pH of the ink is from 7 to 10.

14. A process for printing a substrate with an ink which comprises applying to the substrate an ink which contains a compound of Formula (1) or a salt thereof

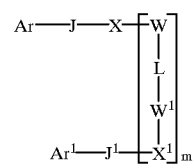

(1)

wherein:

Ar and Ar$^1$ are each, independently, an optionally substituted aromatic group and at least one of Ar and Ar$^1$ carries at least one group selected from —COOH and —PO$_3$H$_2$;

J and J$^1$ are each, independently, —O—, —S—, —NR$^1$— or a group of the Formula (2) or (3):

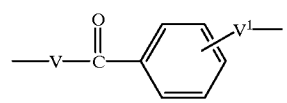

(2)

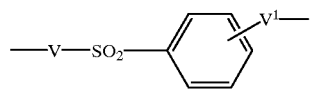

(3)

V and V$^1$ are each, independently, —O—, —S— or —NR$^1$—;

X and X$^1$ are each, independently, a group of the Formula (4), (5) or (6):

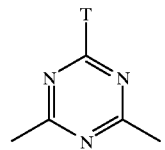

(4)

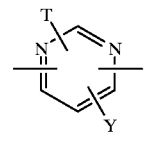

(5)

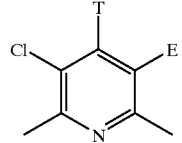

(6)

T is —OR$^2$, —SR$^2$, —NR$^3$R$^4$ a halogen atom, a thiocyano group or a quaternary ammonium group;

Y is H, CN or T;

E is Cl or CN;

each R$^1$ is, independently, H or optionally substituted alkyl;

R², R³ and R⁴ are each, independently, H, alkenyl, substituted alkenyl, alkyl, substituted alkyl, aryl, substituted aryl, aralkyl, substituted aralkyl, cycloalkyl or substituted cycloalkyl, or R³ and R⁴ together with the nitrogen atom to which they are attached form a 5 or 6 membered ring;

W and W¹ are each, independently, —O—, —S—, or —NR⁵— or optionally substituted piperazinylene;

R⁵ is H or optionally substituted alkyl;

L is a divalent organic linking group; or the group —WLW¹— forms an optionally substituted piperazinylene group; and m is 0, 1 or 2.

15. A paper, a textile material, a metal, ceramic or glass substrate printed with an ink as claimed in claim 1.

16. An ink jet printer cartridge containing an ink according to claim 1.

17. A compound of the Formula (1) and salts thereof:

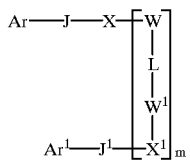

(1)

wherein:

Ar and Ar¹ are each, independently, an optionally substituted aromatic group and at least one of Ar and Ar¹ carries at least one group selected from —COOH and —PO₃H₂;

J and J¹ are each, independently, —O—, —S—, —NR¹— or a group of the Formula (2) or (3):

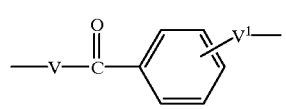

(2)

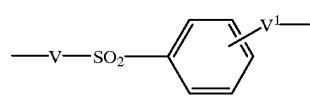

(3)

V and V¹ are each, independently, —O—, —S— or —NR¹—;

X and X¹ are each, independently, a group of the Formula (4), (5) or (6):

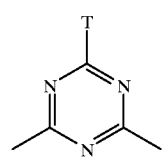

(4)

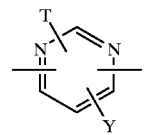

(5)

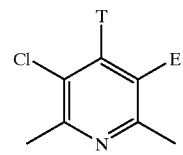

(6)

T is —OR², —SR², —NR³R⁴ a halogen atom, a thiocyano group or a quaternary ammonium group;

Y is H, CN or T;

E is Cl or CN;

each R¹ is, independently, H or optionally substituted alkyl;

R², R³ and R⁴ are each, independently, H, alkenyl, substituted alkenyl, alkyl, substituted alkyl, aryl, substituted aryl, aralkyl, substituted aralkyl, cycloalkyl or substituted cycloalkyl, or R³ and R⁴ together with the nitrogen atom to which they are attached form a 5 or 6 membered ring;

W and W¹ are each, independently, —O—, —S—, or —NR⁵— or optionally substituted piperazinylene;

R⁵ is H or optionally substituted alkyl;

L is a divalent organic linking group; or the group —WLW¹— forms an optionally substituted piperazinylene group; and m is 1 or 2.

18. A compound of the Formula (1) and salts thereof:

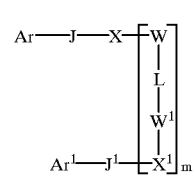

(1)

wherein:

Ar and Ar¹ are each, independently, an optionally substituted aromatic group and at least one of Ar and Ar¹ carries at least one group selected from —COOH and —PO₃H₂;

J and J¹ are each, independently, —O—, —S—, —NR¹— or a group of the Formula (2) or (3):

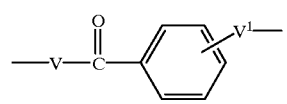

(2)

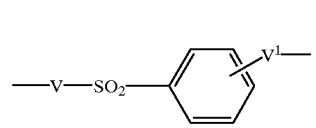

(3)

V and V¹ are each, independently, —O—, —S— or —NR¹—;

X is a group of the Formula (5) or (6):

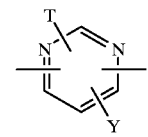
(5)

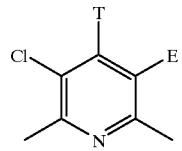
(6)

T is —OR², —SR², —NR³R⁴ a halogen atom, a thiocyano group or a quaternary ammonium group;
Y is H, CN or T;
E is Cl or CN;
each R¹ is, independently, H or optionally substituted alkyl;
R², R³ and R⁴ are each, independently, H, alkenyl, substituted alkenyl, alkyl, substituted alkyl, aryl, substituted aryl, aralkyl, substituted aralkyl, cycloalkyl or substituted cycloalkyl, or R³ and R⁴ together with the nitrogen atom to which they are attached form a 5 or 6 membered ring;
W and W¹ are each, independently, —O—, —S—, or —NR⁵— or optionally substituted piperazinylene;
R⁵ is H or optionally substituted alkyl;
L is a divalent organic linking group; or
the group —WLW¹— forms an optionally substituted piperazinylene group; and
m is 0.

19. A compound of the Formula (1) and salts thereof:

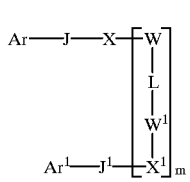
(1)

wherein:
Ar and Ar¹ are each, independently, an optionally substituted aromatic group and at least one of Ar and Ar¹ carries at least one group selected from —COOH and —PO₃H₂;
J and J¹ are each, independently, —O—, —S—, —NR¹— or a group of the Formula (2) or (3):

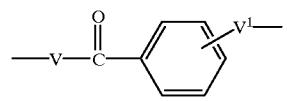
(2)

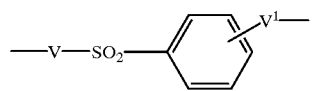
(3)

V and V¹ are each, independently, —O—, —S— or —NR¹—;
X is a group of the Formula (4);

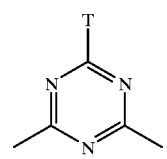
(4)

T is —OR², —SR², —NR³R⁴, a thiocyano group or a quaternary ammonium group;
each R¹, is independently, H or optionally substituted alkyl;
R², R³ and R⁴ are each, independently, H, alkenyl, substituted alkenyl, alkyl, substituted alkyl, aryl, substituted aryl, aralkyl, substituted aralkyl, cycloalkyl or substituted cycloalkyl, or R³ and R⁴ together with the nitrogen atom to which they are attached form a 5 or 6 membered ring; with the proviso that if one of R³ or R⁴ is a substituted aryl, then the other R³ or R⁴ is selected from the group consisting of alkenyl, substituted alkenyl, alkyl, substituted alkyl, aryl, substituted aryl, aralkyl, substituted aralkyl, cycloalkyl or substituted cycloalkyl;
W and W¹ are each, independently, —O—, —S—, or —NR⁵— or optionally substituted piperazinylene;
R⁵ is H or optionally substituted alkyl;
L is a divalent organic linking group; or
the group —WLW¹— forms an optionally substituted piperazinylene group; and
m is 0.

* * * * *